United States Patent [19]

Holtkamp

[11] Plant 4,216

[45] Feb. 21, 1978

[54] AFRICAN VIOLET PLANT

[76] Inventor: Reinhold Holtkamp, Wertherstrasse 112, 4294 Isselburg, Germany

[21] Appl. No.: 746,192

[22] Filed: Nov. 30, 1976

[51] Int. Cl.[2] ..... A01H 5/00

[52] U.S. Cl. ..... Plt./69

[58] Field of Search ..... Plt./69

*Primary Examiner*—Robert E. Bagwill
*Attorney, Agent, or Firm*—Donald D. Jeffery

[57] ABSTRACT

A distinct African Violet plant having strong and erect flower stems, flowers which are medium blue in flower color and relatively large and star-shaped in form, uniform flowering, and generally round, medium green foliage.

2 Drawing Figures

1

The present invention comprises a new and distinct cultivar of African Violet plant, botanically known as *Saintpaulia ionantha,* and hereinafter referred to by the cultivar name Maryland.

Maryland, referred to during the selection process by the designation (b 171/1)-35/76, is a product of a planned breeding program which had the objective of creating a new African violet plant combining certain of the desired characteristics of the parent cultivars. The female, or seed parent, is a non-patented cultivar designated by the breeding No. XX 94 (lilac, 48-8) and was selected for its medium green, round leaves and its upright, strong stems. The male, or pollen parent, also non-patented, is designated by the breeding No. XIX 4339 (red, 46-10), and was selected for breeding because of its red flower color. The cross was made by me in Isselburg, West Germany. The new cultivar Maryland, surprisingly, is generally medium blue in flower color and has star-shaped flowers, which neither parent possesses. However, Maryland does have the desired characteristics from its parents of medium green, generally round leaves and upright, strong stems.

Asexual reproduction of the new cultivar by leaf cuttings and by division of shoots, as performed by me at Isselburg, Rhineland, Germany has demonstrated that the combination of characteristics as herein disclosed for the new cultivar are firmly fixed and are retained through successive generations of asexual reproduction.

The following observations, measurements and values describe plants grown in Isselburg, Rhineland, Germany under greenhouse conditions which closely approximate those generally used in commercial practice.

The following traits have been repeatedly observed and are determined to be basic characteristics of Maryland which in combination distinguish this African Violet as a new and distinct cultivar:

1. Erect, upright and strong flower stems.
2. Compact plant which can be grown close together without stretching leaf stems.
3. Flowers very uniformly, approximately 6–7 weeks after potting.
4. Medium blue flower color and large star-shaped flowers which are non-dropping.
5. Generally round, medium green foliage.

The accompanying photographic drawings show a typical specimen plant of the new cultivar.

Figure 1:
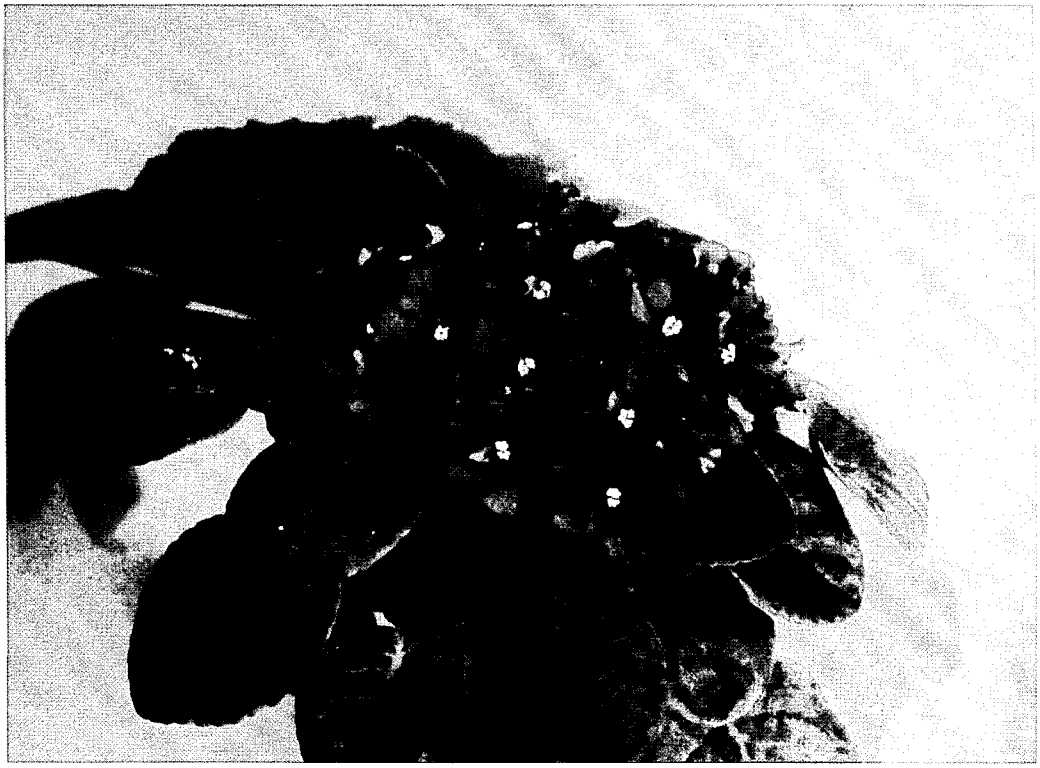

FIG. 1 comprises a perspective view of the finished plant and

2

Figure 2:
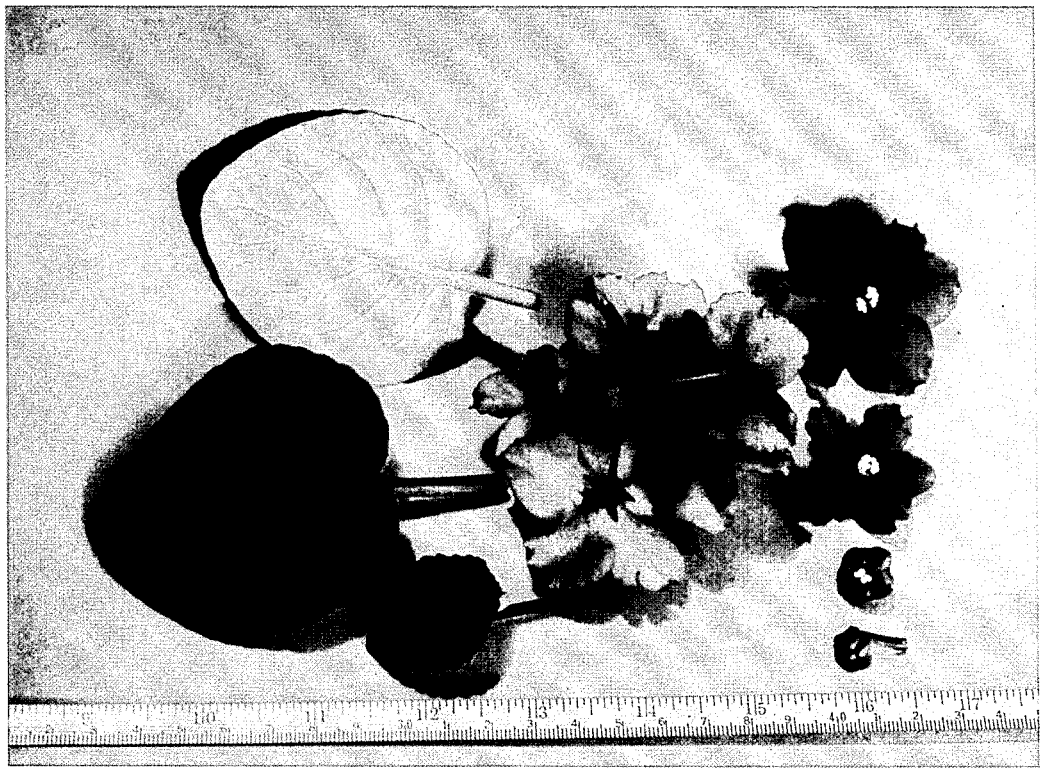

FIG. 2 comprises a photograph showing various parts of the plant, top and underside, and the developing bud formations. The time from the earliest bud formation shown to the fully opened flower is approximately 6–7 weeks. The colors appearing in the photographs are as true as possible with color illustrations of this type.

In the following description, color references are made to the Munsell Limit Color Cascade chart, except where general color terms of ordinary significance are employed.

Botanical classification: *Saintpaulia ionantha,* Ramat. cv Maryland.

Parentage:

*Male parent.*—XIX 4339 red, color 46-10.

*Female parent.*—XX 94 mauve, color 48-8.

Propagation: The new cultivar holds its distinguishing characteristics through successive propagations by leaf cuttings and by division of shoots.

Plant:

*Size.*—From 8 cm. to 10 cm. tall when grown in pots, and approximately 25 cm. in diameter when fully grown.

*Leaves.*—General Form: round to oval. Diameter: 55–60 mm. Texture: soft. Aspect: velvety. Veins: well pronounced on underside. Color: upperside — 21-15. underside — 22-1. Petiole: between light green and reddish; hairy.

*Flowers.*—Buds: cap-shaped red-brown sepals and blue violet outside; 8–10 mm. before opening. Sepals: Color: green-brown to red-brown. Calyx: funnel-shaped and synsepalous. Aspect: hairy outside. Peduncle: 20–30 mm. long, flexible, erect.

*Individual flowers.*—Size: 40–45 mm. Color: Upperside — 1-11. Underside — 1–8. Borne: Profusely in a central flower head forming compact and very upright bouquet. Shape: cup-shaped, open, a few flowers tend to be medium double in shape. Corolla: 5 petals, same size, smooth but waved edges. Arrangement: 5–7 flowers on erect flower stem, ending on receptacle (torus) connected by brown spear-shaped sepals. Flowering time: After potting approximately 6 weeks plant shows the first flowers; a very decorative saleable plant is present in 3 additional weeks.

*Reproductive organs.*—Anthers: 5 anthers with 2 cells, 2 mm. wide; golden yellow color 26-4. Arrangement: basifixed. Filaments: 4–5 mm.

long, light yellow color 25-1. Styles: one, light green, hairy 2 mm., going to violet up to the stigma. Pollen color: 27-2.

*Roots.*—Well developed and fresh while on young and active plants turning brownish on older plants.

*Disease resistance.*—Very good.

General observations: The large flowers of Maryland form a large bouquet on erect and upright stems, thereby providing an early saleable plant. The blooming period is long and the plant continuously blooms, with the stems on second and subsequent bloomings being even stronger than on first blooming. The flowers are non-dropping and the anthers do not spread, thereby giving a tight yellow center. The characteristic of compactness permits the plants to be grown close together, a significant factor to the grower.

I claim:

1. A new and distinct cultivar of African violet known by the cultivar name Maryland and characterized particularly as to uniqueness by the combined characteristics of large star-shaped flowers which are medium blue in flower color and non-dropping; generally round, medium green foliage; erect, upright and strong flower stems; compact growth habit; continuous flowering and very uniform first flowering, approximately 6–7 weeks after potting.

* * * * *